US011090028B2

(12) United States Patent
Wang et al.

(10) Patent No.: US 11,090,028 B2
(45) Date of Patent: Aug. 17, 2021

(54) ULTRASONIC DEVICE AND DEVICE FOR GENERATING MECHANICAL VIBRATION

(71) Applicant: WUXI HISKY MEDICAL TECHNOLOGIES CO., LTD., Wuxi (CN)

(72) Inventors: Qiang Wang, Wuxi (CN); Jinhua Shao, Wuxi (CN); Jin Sun, Wuxi (CN); Houli Duan, Wuxi (CN)

(73) Assignee: WUXI HISKY MEDICAL TECHNOLOGIES CO., LTD., Wuxi (CN)

( * ) Notice: Subject to any disclaimer, the term of this patent is extended or adjusted under 35 U.S.C. 154(b) by 350 days.

(21) Appl. No.: 16/120,180

(22) Filed: Aug. 31, 2018

(65) Prior Publication Data

US 2018/0368808 A1 Dec. 27, 2018

Related U.S. Application Data

(63) Continuation of application No. PCT/CN2017/094030, filed on Jul. 24, 2017.

(30) Foreign Application Priority Data

Aug. 4, 2016 (CN) .......................... 201610634360.6

(51) Int. Cl.
*A61B 8/00* (2006.01)
*A61B 8/08* (2006.01)
*B06B 1/00* (2006.01)

(52) U.S. Cl.
CPC .............. *A61B 8/4494* (2013.01); *A61B 8/00* (2013.01); *A61B 8/085* (2013.01); *A61B 8/429* (2013.01); *A61B 8/485* (2013.01); *B06B 1/00* (2013.01)

(58) Field of Classification Search
CPC ......... A61B 8/4494; A61B 8/00; A61B 8/429; A61B 8/085; A61B 8/485; A61B 8/14; B06B 1/00
See application file for complete search history.

(56) References Cited

U.S. PATENT DOCUMENTS

| 4,947,851 A | 8/1990 | Sarvazyan et al. |
| 5,078,013 A | 1/1992 | Kuramochi |
| (Continued) | | |

FOREIGN PATENT DOCUMENTS

| CN | 201408181 Y | 2/2010 |
| CN | 101869490 A | 10/2010 |
| (Continued) | | |

OTHER PUBLICATIONS

The International Search Report of corresponding International PCT Application No. PCT/CN2017/094030, dated Oct. 19, 2017.
(Continued)

*Primary Examiner* — Christopher Koharski
*Assistant Examiner* — Kaitlyn E Selmer
(74) *Attorney, Agent, or Firm* — J.C. Patents

(57) ABSTRACT

Provided are an ultrasonic device and a device for generating mechanical vibration. The ultrasonic device includes an ultrasonic probe and the device for generating mechanical vibration, where the device for generating mechanical vibration includes a vibration generator (1), a damping component (2), and a pressure component (3); the damping component (2) is fixed between the vibration generator (1) and the pressure component (3); the ultrasonic probe is connected to the pressure component (3); and the vibration generator (1) is configured to generate a vibration when a pressure value detected by the pressure component (3) falls into a preset range.

18 Claims, 3 Drawing Sheets

(56) References Cited

U.S. PATENT DOCUMENTS

| | | | |
|---|---|---|---|
| 6,168,572 B1 | 1/2001 | Vexier et al. | |
| 8,487,513 B2* | 7/2013 | Park | B06B 1/0644 310/326 |
| 2005/0085728 A1 | 4/2005 | Fukuda | |
| 2008/0237953 A1* | 10/2008 | Tanaka | F16F 1/3849 267/141 |
| 2009/0306515 A1* | 12/2009 | Matsumura | A61B 8/4281 600/459 |
| 2012/0271166 A1 | 10/2012 | Shao | |
| 2012/0316407 A1 | 12/2012 | Anthony et al. | |
| 2014/0094701 A1 | 4/2014 | Kwartowitz et al. | |
| 2014/0114193 A1 | 4/2014 | Anthony et al. | |

FOREIGN PATENT DOCUMENTS

| | | |
|---|---|---|
| CN | 103006267 A | 4/2013 |
| CN | 103006268 A | 4/2013 |
| CN | 203000987 U | 6/2013 |
| CN | 103720490 A | 4/2014 |
| CN | 103006268 B | 6/2014 |
| CN | 204439255 U | 7/2015 |
| CN | 204439256 U | 7/2015 |
| CN | 105067180 A | 11/2015 |
| CN | 105395218 A | 3/2016 |
| CN | 105640593 A | 6/2016 |
| CN | 106264605 A | 1/2017 |
| CN | 206303913 U | 7/2017 |
| DE | 10 2009 022 187 A1 | 11/2010 |
| KR | 1020100055677 A | 5/2010 |
| KR | 1020150045045 A | 4/2015 |
| RU | 2419388 C2 | 5/2011 |
| TW | 201618721 | 6/2016 |
| WO | WO2010143555 | 12/2010 |
| WO | WO2019133888 A2 | 7/2019 |

OTHER PUBLICATIONS

The Chinese First Examination Report of corresponding China patent application No. 201610634360.6, dated May 3, 2018.
The Chinese Second Examination Report of corresponding China patent application No. 201610634360.6, dated Dec. 4, 2018.
The Notice of Allowance of KR application No. 10-2019-7006355.
The Notice of Allowance of CN application No. 201610634360.6.
The extended European Search Report of corresponding European application No. 17 83 6306, dated Oct. 9, 2019.
The Australian Examination Report No. 1 for standard patent application corresponding to Australian application No. 2017305286, dated Mar. 27, 2019.
The Japanese Examination Report of corresponding Japanese application No. 2018-555542, dated Oct. 2, 2019.
The Russian Federation Examination Report of corresponding Russian application No. 20191057371/14(010860), dated Aug. 15, 2019.
Second OA of the parallel CA application.
Notice of Allowance of the parallel JP application.

* cited by examiner

ULTRASONIC DEVICE AND DEVICE FOR GENERATING MECHANICAL VIBRATION

CROSS-REFERENCE TO RELATED APPLICATIONS

This present application is a continuation of International Application No. PCT/CN2017/094030, filed on Jul. 24, 2017, which claims priority to Chinese Patent Application No. 201610634360.6, filed on Aug. 4, 2016, both of which are hereby incorporated by reference in their entireties.

TECHNICAL FIELD

The present disclosure relates to the technical field of organ detection and, in particular, to an ultrasonic device and a device for generating mechanical vibration.

BACKGROUND

Each organ of a human or animal body has a certain elasticity. If an organ undergoes a fibrosis lesion, its elasticity value will change, and different degrees of fibrosis correspond to different changes in the elasticity values. Therefore, a symptomatic treatment may be performed by detecting the elasticity value of an organ to diagnose a degree of organ fibrosis.

The method of detecting the elasticity value for the organs of the human or animal body in the prior art lies in: removing a living organism of an organ through a surgical operation, then conducting an elasticity detection for the removed living organism, and performing a treatment according to the detection result. However, the entire process of removing a living organism through the surgery takes longer time and causes a wound on the human or animal body, which inevitably makes the human or animal suffering more. Therefore, the prior art is short of a means for detecting the elasticity of organs that is safe and harmless to the human or animal body.

SUMMARY

The present disclosure provides an ultrasonic device and a device for generating mechanical vibration to achieve the purpose of detecting the elasticity of organs without a surgical operation.

In a first aspect, the present disclosure provides an ultrasonic device, including: an ultrasonic probe and a device for generating mechanical vibration, where the device for generating mechanical vibration includes a vibration generator, a damping component, and a pressure component;

the damping component is fixed between the vibration generator and the pressure component; the ultrasound probe is connected to the pressure component; and the vibration generator is configured to generate a vibration when a pressure value detected by the pressure component falls into a preset range.

In an embodiment of the present disclosure, the damping component includes a tubular bracket that is open-ended, an upper resilient piece, a lower resilient piece, and a linkage;

where a lower surface of the upper resilient piece is connected to an upper end of the tubular bracket, and an upper surface of the upper resilient piece is connected to the pressure component;

an upper surface of the lower resilient piece is connected to a lower end of the tubular bracket, and a lower surface of the lower resilient piece is connected to the vibration generator; and the linkage is arranged inside the tubular bracket and extends in the direction of a force of the vibration generator, both ends of the linkage are fixedly connected to the lower surface of the upper resilient piece and the upper surface of the lower resilient piece, respectively.

In an embodiment of the present disclosure, the tubular bracket is made of elastic material.

In an embodiment of the present disclosure, the upper resilient piece and the lower resilient piece are made of rubber material or plastic.

In an embodiment of the present disclosure, the vibration generator includes:

a vibration bracket, a first vibrator and a second vibrator;

the vibration bracket has a concave structure, and both arms of a slot of the concave structure are engaged with sidewalls of the tubular bracket;

the second vibrator is fixedly accommodated at a bottom of the concave structure, and the second vibrator is provided with a chute facing the lower resilient piece, and an extending direction of the chute is the same as that of the linkage;

the first vibrator is accommodated on a top of the concave structure, the first vibrator is provided with a slide bar at its lower surface facing the chute, and an upper surface of the first vibrator is fixedly connected to the lower surface of the lower resilient piece; and the slide bar of the first vibrator is slid-ably arranged in the chute of the second vibrator so that the first vibrator slides up and down under an external force.

In an embodiment of the present disclosure, there are two chutes symmetrically arranged on the second vibrator and, correspondingly, there are two slide bars engaged with the chutes.

In an embodiment of the present disclosure, the pressure component includes: a pressure sensor and a sensor holder;

the sensor holder is fixed at one end of the damping component, the pressure sensor is fixed on the sensor holder, and the other end of the damping component is connected to the vibration generator.

In an embodiment of the present disclosure, the sensor holder is provided with a fixing groove, and the pressure sensor is embedded in the fixing groove and protrudes from a plane of an opening of the fixing groove.

In an embodiment of the present disclosure, the preset range of the pressure value is 3.7N~4.1N.

According to the ultrasonic device provided in the present disclosure, an ultrasonic probe and a device for generating mechanical vibration connected thereto are arranged, where the device for generating mechanical vibration is provided with a vibration generator, a damping component and a pressure component connected sequentially, and the ultrasonic probe is connected to the pressure component. During detection, the ultrasonic probe is brought into contact with the skin surface corresponding to an organ to be detected, and a downward pressure is applied to the skin surface. When a pressure value detected by the pressure component falls into a preset range, an electrical signal is transmitted to the vibration generator by an external electrical signal output device, such that the vibration generator generates a vibration and the damping component is driven to deform. Upon being deformed, the damping component is reset under its own elastic force to generate a certain mechanical vibration, therefore, when a detection is conducted on elasticity for an organ of a human or animal body, a certain mechanical vibration may be generated outside the organ to be detected by using the device, that is, the mechanical vibration is generated outside the human body or the animal body, to which no damage or injury is caused. When the device for generating mechanical vibration generates the vibration, an ultrasonic wave is transmitted through the ultrasonic probe to the organ to be detected for the human or animal body. Since the propagation speed of the ultrasonic wave is far greater than the propagation speed of the mechanical wave, a wave velocity value of the mechanical wave generated from the vibration of the device for generating mechanical vibration is detected through the ultrasonic wave, and an elasticity value of the organ to be detected is calculated through the wave velocity value. Thus, the degree of fibrosis of the organ to be detected is determined, therefore, the purpose of detecting elasticity for the organ is achieved through operations on the skin surface of the human or animal body, and the defect in the prior art that the detection needs to be performed only by a surgical operation is overcome. The entire detection process is fast and convenient. Moreover, since the vibration generator performs an action under the condition that a pressure value detected by the pressure component falls into a preset range, and the mechanical vibration wave generated by the device has a stable frequency due to the elastic reset from the damping component, the accuracy of result of the elasticity detection is ensured.

In a second aspect, the present disclosure provides a device for generating mechanical vibration, including: a vibration generator, a damping component and a pressure component;

where the damping component is fixed between the vibration generator and the pressure component; the vibration generator is configured to generate a vibration when a pressure value detected by the pressure component falls into a preset range.

According to the device for generating mechanical vibration provided in the present disclosure, a vibration generator, a damping component and a pressure component are provided, which are sequentially connected. When a pressure value detected by the pressure component falls into a preset range, an electrical signal is transmitted to the vibration generator by an external electrical signal output device, such that the vibration generator generates a vibration and the damping component is driven to be deformed. Upon being deformed, the damping component is reset under its own elastic force to generate a certain mechanical vibration, therefore, when a detection is conducted on elasticity of an organ of a human or animal body, a certain mechanical vibration may be generated outside the organ to be detected by using the device, that is, the mechanical vibration is generated outside the human or the animal body, to which no damage or injury is caused, and it is very convenient to use; moreover, since the vibration generator performs an action under the condition that a pressure value detected by the pressure component falls into a preset range, and the mechanical vibration wave generated by the device has a stable frequency due to a reset from the elasticity of the damping component, thereby ensuring the accuracy of result of the elasticity detection.

BRIEF DESCRIPTION OF DRAWINGS

In order to describe technical solutions in embodiments of the present disclosure or in the prior art more clearly, accompanying drawings used for description of the embodiments or the prior art will be briefly described hereunder. Obviously, the described drawings below are some embodiments of the present disclosure. For persons of ordinary skill in the art, other drawings may be obtained based on these drawings without any creative effort.

DESCRIPTION OF NUMERICAL REFERENCES

1: vibration generator;
2: damping component;
3: pressure component;
11: vibration bracket;
12: first vibrator;
121: slide bar;
13: second vibrator;
131: chute;
21: tubular bracket;
22: upper resilient piece;
23: lower resilient piece;
31: sensor holder;
32: pressure sensor;
311: fixing groove;
312: lug boss.

DESCRIPTION OF EMBODIMENTS

In order to make objectives, technical solutions, and advantages of embodiments of the present disclosure clearer, the technical solutions in the embodiments of the present disclosure will be described hereunder clearly and completely with reference to accompanying drawings in the embodiments of the present disclosure. Obviously, the described embodiments are only a part of the embodiments of the present disclosure, rather than all embodiments of the present disclosure. All other embodiments obtained by persons of ordinary skill in the art based on the embodiments of the present disclosure without any creative effort shall fall into the protection scope of the present disclosure.

Embodiment 1

Figure 1:
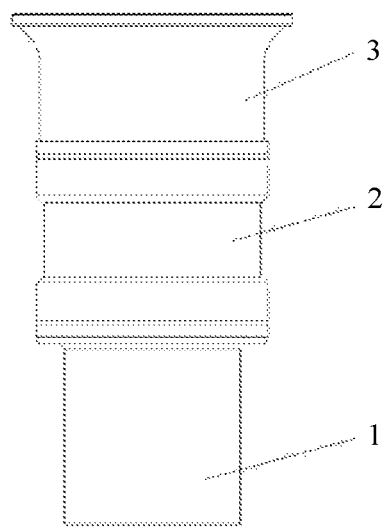
FIG. 1 is a simplified schematic structural view of a device for generating mechanical vibration in an ultrasonic device according to an embodiment of the present disclosure.
Figure 2:
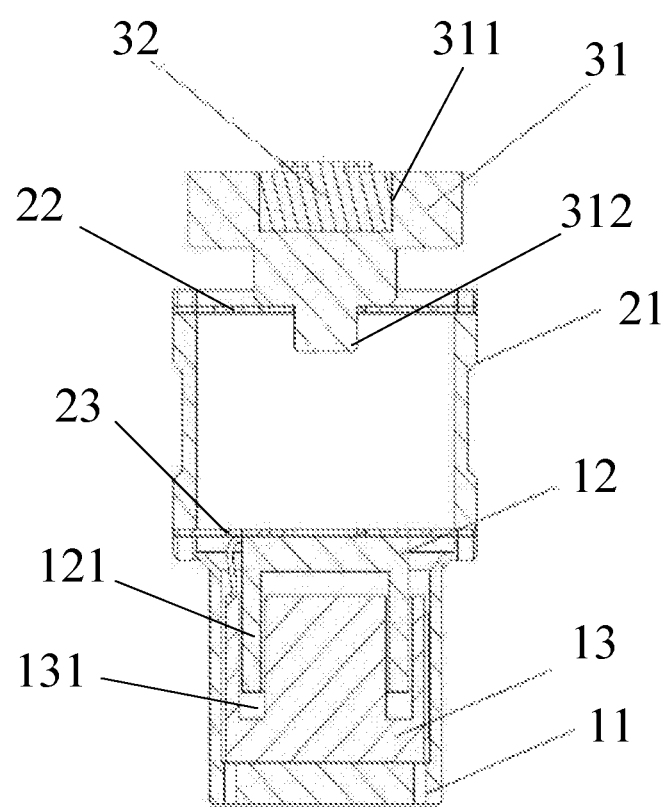
FIG. 2 is a schematic cross-sectional view of the device for generating mechanical vibration of FIG. 1 in an initial state.
Figure 3:
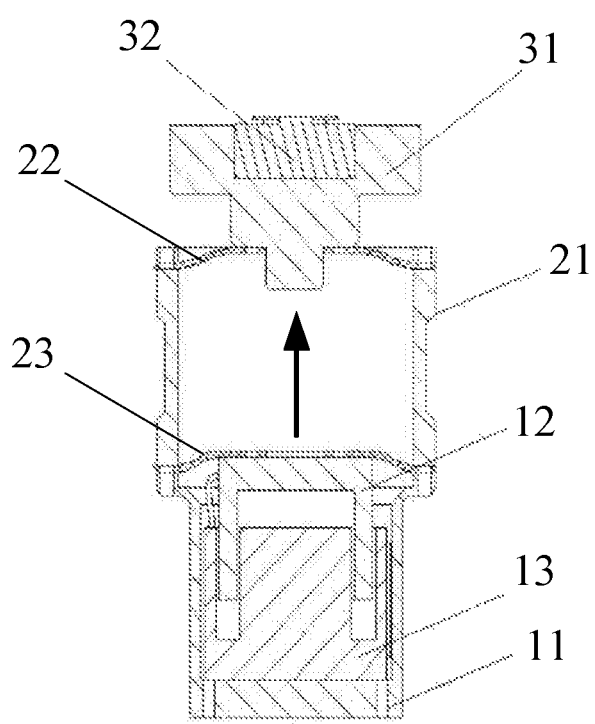
FIG. 3 is a schematic cross-sectional view of the device for generating mechanical vibration of FIG. 1 at a time when an instantaneous vibration occurs.

FIG. 1 is a simplified schematic structural view of a device for generating mechanical vibration in an ultrasonic device according to an embodiment of the present disclosure. FIG. 2 is a schematic cross-sectional view of the device for generating mechanical vibration of FIG. 1 in an initial state. FIG. 3 is a schematic cross-sectional view of the device for generating mechanical vibration of FIG. 1 at a time when an instantaneous vibration occurs. With reference to FIG. 1~FIG. 3, this embodiment provides an ultrasonic device, including: an ultrasonic probe (not shown in the drawings) and a device for generating mechanical vibration. The device for generating mechanical vibration includes: a vibration generator 1, a damping component 2, and a pressure component 3. Among them, the damping component 2 is fixed between the vibration generator 1 and the pressure component 3, and the ultrasonic probe is connected to the pressure component 3. The vibration generator 1 is configured to generate a vibration when a pressure value detected by the pressure component 3 falls into a preset range.

In use, the ultrasonic probe of the ultrasonic device is brought into contact with the skin surface corresponding to a position of an organ of the human or animal body to be detected, and a downward pressure is applied to the skin surface. When a pressure value detected by the pressure component 3 falls into a preset range, an electrical signal is transmitted to the vibration generator 1 by an external electrical signal output device, such that the vibration generator 1 generates a vibration, which drives the damping component 2 to be deformed, and upon being deformed, the damping component 2 is reset under its own elastic force to generate a certain mechanical vibration, that is, a mechanical vibration is generated outside the organ to be detected. When the mechanical vibration is generated, an ultrasonic wave is transmitted through the ultrasonic probe to the organ to be detected. Since the speed of the ultrasonic wave is greater than the propagation speed of the mechanical wave, a wave velocity value of the mechanical wave is detected through the ultrasonic wave, an elasticity value of the organ to be detected is calculated through the wave velocity value, and the degree of fibrosis of the organ to be detected is determined according to the elasticity value.

Since different persons or animals are different in fat thickness and cortex tightness, different pressures are required in measuring elasticity of organs in the human or animal body. The detection result would be accurate only when a pressure value applied to an organ falls into a corresponding pressure range of the organ. Therefore, for different organs to be detected, a pressure range required for the organ to be detected needs to be set in advance, and a pressure value applied to the organs to be detected is detected by the pressure component 3 to ensure that the pressure applied to the organs falls into the set range, thus, the accuracy of the detection result is ensured. Exemplarily, in this embodiment, the preset range of the pressure value is 3.7N~4.1N. For instance, when the pressure value detected by the pressure component 3 is 3.9N, the vibration generator 1 will generate a vibration. The preset ranges of the pressure value may be particularly set according to different organs.

According to the ultrasonic device provided in this embodiment, an ultrasonic probe and a device for generating mechanical vibration connected thereto are arranged, where the device for generating mechanical vibration is provided with a vibration generator, a damping component and a pressure component connected sequentially, and the ultrasonic probe is connected to the pressure component. During detection, the ultrasonic probe is brought into contact with the skin surface corresponding to an organ to be detected, and a downward pressure is applied to the skin surface. When a pressure value detected by the pressure component falls into a preset range, an electrical signal is transmitted to the vibration generator by an external electrical signal output device, such that the vibration generator generates a vibration and the damping component is driven to deform. Upon being deformed, the damping component is reset under its own elastic force to generate a certain mechanical vibration, therefore, when a detection is conducted on elasticity for an organ of a human or animal body, a certain mechanical vibration may be generated outside the organ to be detected by using the device, that is, the mechanical vibration is generated outside the human body or the animal body, to which no damage or injury is caused. When the device for generating mechanical vibration generates the vibration, an ultrasonic wave is transmitted through the ultrasonic probe to the organ to be detected for the human or animal body. Since the propagation speed of the ultrasonic wave is far greater than the propagation speed of the mechanical wave, a wave velocity value of the mechanical wave generated from the vibration of the device for generating mechanical vibration is detected through the ultrasonic wave, and an elasticity value of the organ to be detected is calculated through the wave velocity value. Thus, the degree of fibrosis of the organ to be detected is determined, therefore, the purpose of detecting elasticity for the organ is achieved through operations on the skin surface of the human or animal body, and the defect in the prior art that the detection needs to be performed only by a surgical operation is overcome. The entire detection process is fast and convenient. Moreover, since the vibration generator performs an action under the condition that a pressure value detected by the pressure component falls into a preset range, and the mechanical vibration wave generated by the device has a stable frequency due to the elastic reset from the damping component, the accuracy of result of the elasticity detection is ensured.

In this embodiment, the damping component 2 includes: a tubular bracket 21 that is open-ended, an upper resilient piece 22, a lower resilient piece 23, and a linkage (not shown in the drawings). A lower surface of the upper resilient piece 22 is connected to an upper end of the tubular bracket 21, and an upper surface of the upper resilient piece 22 is connected to the pressure component 3. An upper surface of the lower resilient piece 23 is connected to a lower end of the tubular bracket 21, and a lower surface of the lower resilient piece 23 is connected to the vibration generator 1. The linkage (not shown in the drawings) is arranged inside the tubular bracket 21 and extends in the direction of a force of the vibration generator 1, both ends of the linkage are fixedly connected to the lower surface of the upper resilient piece 22 and the upper surface of the lower resilient piece 23, respectively. In a specific implementation, the tubular bracket 21 may be made of elastic material, and the upper resilient piece 22 and the lower resilient piece 23 may be made of rubber material or plastic.

The vibration generator 1 specifically includes: a vibration bracket 11, a first vibrator 12, and a second vibrator 13. The vibration bracket 11 has a concave structure, both arms of a slot of the concave structure are engaged with sidewalls of the tubular bracket 21. The second vibrator 13 is fixedly accommodated at a bottom of the concave structure, and the second vibrator 13 is provided with a chute 131 facing the lower resilient piece 23, and an extending direction of the chute 131 is the same as that of the linkage (not shown in the drawings). The first vibrator 12 is accommodated on a top of the concave structure, the first vibrator 12 is provided with a slide bar 121 at its lower surface facing the chute 131, and an upper surface of the first vibrator 12 is fixedly connected to the lower surface of the lower resilient piece 23. The slide bar 121 of the first vibrator 12 is arranged in the chute 131 of the second vibrator 13 so that the first vibrator 12 slides up and down under an external force. Specifically, the first vibrator 12 is connected to an external electrical signal output device, and the electrical signal output device outputs an electrical signal so that the first vibrator 12 can slide upward along the chute 131. The upward direction herein refers to a direction facing the damping component 2.

More preferably, there are two chutes 131 symmetrically arranged on the second vibrator 13, and there are two slide bars 121 engaged with the chutes 131. Herein, the number of the chutes and the slide bars is set to two only for illustrative purposes. The specific number of the chutes and the slide bars is not limited in the present disclosure, and the specific number thereof may be set according to practical use requirements.

The first vibrator 12 and the second vibrator 13 in this embodiment may be motors or other components that can generate vibrations, which is not limited in the present disclosure.

The pressure component 3 specifically includes: a sensor holder 31 and a pressure sensor 32, where the sensor holder 31 is fixed at one end of the damping component 2, the pressure sensor 32 is fixed on the sensor holder 31, and the other end of the damping component 2 is connected to the vibration generator 1.

In a specific implementation, the sensor holder 31 may be provided with a fixing groove 311, the pressure sensor 32 is embedded in the fixing groove 311, and the top of the pressure sensor 32 protrudes from a plane of an opening of the fixing groove 311. The sensor holder 31 may also be provided with a lug boss 312 at its lower surface, and the upper resilient piece 22 may be provided in an annular structure. The lug boss 312 may penetrate into the annular center of the upper resilient piece 22 for a matched engagement.

Based on the above embodiments, the following further describes the ultrasonic device according to this embodiment through a specific process of detecting elasticity of an organ of the human or animal body:

The ultrasonic probe is installed at the front end of the pressure sensor 32. The ultrasonic probe is brought into contact with the skin surface corresponding to an organ of the human or animal body to be detected. Then, a downward pressure is applied to the skin surface through the device in this embodiment, and the pressure sensor 32 detects a specific pressure value applied to the skin surface. Upon the pressure value falls into a preset range, an electrical signal is transmitted to the vibration generator 1 by an external electrical signal output device, such that the first vibrator 12 and the second vibrator 13 of the vibration generator are subject to a displacement movement. Specifically, the external electrical signal output device is electrically connected to the first vibrator 12. When the first vibrator 12 receives an electrical signal, the first vibrator 12 moves upward along the chute 131. Since the lower resilient piece 23 is connected to the first vibrator 12, the first vibrator 12 moves upward to give an upward pushing force to the lower resilient piece 23, so that the lower resilient piece 23 is deformed, that is, the lower resilient piece 23 is bent towards the direction of the pressure sensor. Meanwhile, since both ends of the linkage are fixedly connected to the upper resilient piece 22 and the lower resilient piece 23 respectively, the linkage drives the upper resilient piece 22 to be deformed under the upward force of the lower resilient piece 23, so that the pressure sensor 32 and the ultrasonic probe in contact with the skin press against the skin. Due to elastic forces of the upper resilient piece 22 and the lower resilient piece 23 in themselves, the upper resilient piece 22 and the lower resilient piece 23 are subsequently reset under their own elastic forces, that is, the upper resilient piece 22 and the lower resilient piece 23 move downward, that is, the slide bar of the first vibrator 12 moves downward along the chute of the second vibrator 13 until the upper resilient piece 22 and the lower resilient piece 23 are reset to their initial states. Therefore, a certain mechanical vibration is generated outside the organ to be detected, and a mechanical wave at a certain frequency is generated. An ultrasonic wave is transmitted through the ultrasonic probe to the organ of the human or animal body to be detected. Since the propagation speed of the ultrasonic wave is far greater than that of the mechanical wave, a wave velocity value of the mechanical wave generated above is detected through the ultrasonic wave, and an elasticity value of the organ is calculated through the wave velocity value of the mechanical wave. Thus, the degree of fibrosis of the organ of the human or animal body is determined. Moreover, since the first vibrator generates a vibration under the condition that a pressure value detected by the pressure sensor falls into a preset range, and the mechanical wave generated on the organ to be detected is a mechanical wave at a stable frequency due to the elastic reset functions in the upper and lower resilient pieces themselves, the waveform of the mechanical wave is more accurate, and the accuracy of results for the elasticity detection is ensured.

Embodiment 2

This embodiment provides a device for generating mechanical vibration, including: a vibration generator 1, a damping component 2, and a pressure component 3. The damping component 2 is fixed between the vibration generator 1 and the pressure component 3; and the vibration generator 1 is configured to generate a vibration when a pressure value detected by the pressure component 3 falls into a preset range.

The device for generating mechanical vibration provided in this embodiment has a same structure as that of the device for generating mechanical vibration in the ultrasonic device provided in Embodiment 1, and the same technical effect can be achieved, which will not be repeated herein again.

According to the device for generating mechanical vibration provided in this embodiment, a vibration generator, a damping component and a pressure component are provided, which are sequentially connected. When a pressure value detected by the pressure component falls into a preset range, an electrical signal is transmitted to the vibration generator by an external electrical signal output device, such that the vibration generator generates a vibration and the damping component is driven to be deformed. Upon being deformed, the damping component is reset under its own elastic force to generate a certain mechanical vibration. Therefore, when a detection is conducted on elasticity for an organ of a human or animal body, a certain mechanical vibration may be generated outside the organ to be detected by using the device. That is, a certain mechanical vibration may be generated outside the organ of the human or animal body to be detected through operations on the skin surface of the human or animal body, to which no damage or injury is caused, and it is very convenient to use; moreover, since the vibration generator performs an action under the condition that a pressure value detected by the pressure component falls into a preset range, and the mechanical vibration wave generated by the device has a stable frequency due to the elastic reset from the damping component, the accuracy of result of the elasticity detection is ensured.

Finally, it should be noted that each of the above embodiments is only used to illustrate the technical solutions of the present disclosure, rather than limiting them; although the present disclosure has been illustrated in detail with reference to each of the foregoing embodiments, persons of ordinary skill in the art should understand that: they may still modify the technical solutions described in the foregoing embodiments or equivalently replace some or all of the technical features; however, these modifications or replacements do not make the essence of the corresponding technical solutions depart from the scope of the technical solutions in each of the embodiments of the present disclosure.

What is claimed is:

1. An ultrasonic device, comprising: an ultrasonic probe and a device for generating mechanical vibration, wherein the device for generating mechanical vibration comprises a vibration generator, a damping component, and a pressure component;
the damping component is fixed between the vibration generator and the pressure component; the ultrasound probe is connected to the pressure component,
wherein the damping component comprises a tubular bracket that is open-ended, an upper resilient piece, a lower resilient piece, and a linkage;
wherein a lower surface of the upper resilient piece is connected to an upper end of the tubular bracket, and an upper surface of the upper resilient piece is connected to the pressure component;
an upper surface of the lower resilient piece is connected to a lower end of the tubular bracket, and a lower surface of the lower resilient piece is connected to the vibration generator; and
the linkage is arranged inside the tubular bracket and extends in the direction of a force of the vibration generator, both ends of the linkage are fixedly connected to the lower surface of the upper resilient piece and the upper surface of the lower resilient piece, respectively,
wherein the vibration generator is configured to generate a vibration which drives the upper resilient piece and the lower resilient piece of the damping component to be deformed, when a pressure value detected by the pressure component falls into a preset range, upon being deformed, the upper resilient piece and the lower resilient piece of the damping component are reset under its own elastic force to generate a mechanical vibration outside the organ to be detected.

2. The ultrasonic device according to claim 1, wherein the tubular bracket is made of elastic material.

3. The ultrasonic device according to claim 1, wherein the upper resilient piece and the lower resilient piece are made of rubber material or plastic.

4. The ultrasonic device according to claim 1, wherein the vibration generator comprises:
a vibration bracket, a first vibrator and a second vibrator;
the vibration bracket has a concave structure, and both arms of a slot of the concave structure are engaged with sidewalls of the tubular bracket;
the second vibrator is fixedly accommodated at a bottom of the concave structure, the second vibrator is provided with a chute facing the lower resilient piece, and an extending direction of the chute is the same as that of the linkage;
the first vibrator is accommodated on a top of the concave structure, the first vibrator is provided with a slide bar at its lower surface facing the chute, and an upper surface of the first vibrator is fixedly connected to the lower surface of the lower resilient piece; and
the slide bar of the first vibrator is slid-ably arranged in the chute of the second vibrator, so that the first vibrator slides up and down under an external force.

5. The ultrasonic device according to claim 2, wherein the vibration generator comprises:
a vibration bracket, a first vibrator and a second vibrator;
the vibration bracket has a concave structure, and both arms of a slot of the concave structure are engaged with sidewalls of the tubular bracket;
the second vibrator is fixedly accommodated at a bottom of the concave structure, the second vibrator is provided with a chute facing the lower resilient piece, and an extending direction of the chute is the same as that of the linkage;
the first vibrator is accommodated on a top of the concave structure, the first vibrator is provided with a slide bar at its lower surface facing the chute, and an upper surface of the first vibrator is fixedly connected to the lower surface of the lower resilient piece; and
the slide bar of the first vibrator is slid-ably arranged in the chute of the second vibrator, so that the first vibrator slides up and down under an external force.

6. The ultrasonic device according to claim 3, wherein the vibration generator comprises:
a vibration bracket, a first vibrator and a second vibrator;
the vibration bracket has a concave structure, and both arms of a slot of the concave structure are engaged with sidewalls of the tubular bracket;
the second vibrator is fixedly accommodated at a bottom of the concave structure, the second vibrator is provided with a chute facing the lower resilient piece, and an extending direction of the chute is the same as that of the linkage;
the first vibrator is accommodated on a top of the concave structure, the first vibrator is provided with a slide bar at its lower surface facing the chute, and an upper surface of the first vibrator is fixedly connected to the lower surface of the lower resilient piece; and
the slide bar of the first vibrator is slid-ably arranged in the chute of the second vibrator, so that the first vibrator slides up and down under an external force.

7. The ultrasonic device according to claim 4, wherein there are two chutes symmetrically arranged on the second vibrator and, correspondingly, there are two slide bars engaged with the chutes.

8. The ultrasonic device according to claim 1, wherein the pressure component comprises: a pressure sensor and a sensor holder; and
the sensor holder is fixed at one end of the damping component, the pressure sensor is fixed on the sensor holder, and the other end of the damping component is connected to the vibration generator.

9. The ultrasonic device according to claim 1, wherein the pressure component comprises: a pressure sensor and a sensor holder; and
the sensor holder is fixed at one end of the damping component, the pressure sensor is fixed on the sensor holder, and the other end of the damping component is connected to the vibration generator.

10. The ultrasonic device according to claim 2, wherein the pressure component comprises: a pressure sensor and a sensor holder; and
the sensor holder is fixed at one end of the damping component, the pressure sensor is fixed on the sensor holder, and the other end of the damping component is connected to the vibration generator.

11. The ultrasonic device according to claim 3, wherein the pressure component comprises: a pressure sensor and a sensor holder; and
the sensor holder is fixed at one end of the damping component, the pressure sensor is fixed on the sensor holder, and the other end of the damping component is connected to the vibration generator.

12. The ultrasonic device according to claim 8, wherein the sensor holder is provided with a fixing groove, and the pressure sensor is embedded in the fixing groove and protrudes from a plane of an opening of the fixing groove.

13. The ultrasonic device according to claim 1, wherein the preset range of the pressure value is 3.7N-4.1N.

14. The ultrasonic device according to claim 2, wherein the preset range of the pressure value is 3.7N-4.1N.

15. The ultrasonic device according to claim 3, wherein the preset range of the pressure value is 3.7N-4.1N.

16. A device for generating mechanical vibration, comprising: a vibration generator, a damping component and a pressure component;

wherein the damping component is fixed between the vibration generator and the pressure component, wherein a lower surface of the upper resilient piece is connected to an upper end of the tubular bracket, and an upper surface of the upper resilient piece is connected to the pressure component;

an upper surface of the lower resilient piece is connected to a lower end of the tubular bracket, and a lower surface of the lower resilient piece is connected to the vibration generator; and the linkage is arranged inside the tubular bracket and extends in the direction of a force of the vibration generator, both ends of the linkage are fixedly connected to the lower surface of the upper resilient piece and the upper surface of the lower resilient piece, respectively, wherein the vibration generator is configured to generate a vibration which drives the upper resilient piece and the lower resilient piece of the damping component to be deformed, when a pressure value detected by the pressure component falls into a preset range, upon being deformed, the upper resilient piece and the lower resilient piece of the damping component are reset under its own elastic force to generate a mechanical vibration outside the organ to be detected.

17. The ultrasonic device according to claim 1, wherein the lower surface of the upper resilient piece is directly connected to the upper end of the tubular bracket, and the upper surface of the lower resilient piece is directly connected to the lower end of the tubular bracket.

18. The device for generating mechanical vibration according to claim 16, wherein the lower surface of the upper resilient piece is directly connected to the upper end of the tubular bracket, and the upper surface of the lower resilient piece is directly connected to the lower end of the tubular bracket.

* * * * *